United States Patent [19]

Degonde et al.

[11] 4,137,908

[45] Feb. 6, 1979

[54] APPARATUS FOR OBSERVING CARDIAC RHYTHM FREE OF INTERFERING EFFECTS

[75] Inventors: Jean Degonde, Orsay; Régis Freschard, Meudon-la-Foret; Louis de Poulepiquet, Orsay, all of France

[73] Assignee: Assistance Technique Medicale Serdal S.A. Societe anonyme, Maurepas, France

[21] Appl. No.: 765,657

[22] Filed: Feb. 4, 1977

[51] Int. Cl.² .............................................. A61B 5/04
[52] U.S. Cl. ........................ 128/2.06 R; 128/2.06 F; 128/2.1 Z; 128/419 PT
[58] Field of Search ..................... 128/2.05 T, 2.06 A, 128/2.06 F, 2.06 R, 2.1 Z, 419 PT

[56] References Cited

U.S. PATENT DOCUMENTS

| | | | |
|---|---|---|---|
| 3,677,261 | 7/1972 | Day ................................... | 128/2.1 Z |
| 3,716,059 | 2/1973 | Welborn et al. ................... | 128/2.1 Z |
| 3,742,936 | 7/1973 | Blanie et al. ...................... | 128/2.1 Z |
| 3,782,367 | 1/1974 | Hochberg et al. ............. | 128/2.06 A |

Primary Examiner—William E. Kamm
Attorney, Agent, or Firm—William R. Woodward

[57] ABSTRACT

A cardiac rhythm observation apparatus that separates and then provides for correlation of cardiographic and electrocardiographic signals has four electrodes for attachment to the chest of a subject. Two of the electrodes connect a high-frequency current for application to the subject. The other two electrodes disposed between the first two are connected to a channel for detecting, filtering and forming a rheocardiographic signal, which channel is connected to a heartbeat counter proper. A channel for eliminating variations in pulmonary impedance is connected to the feed electrodes and delivers a pulmonary rheographic signal to a stage in the detecting channel in which the pulmonary rheographic signal is substracted from the raw rheographic signal. A correlation stage is provided for correlation either with the separated electrocardiographic signal or with stimulation pulses.

4 Claims, 3 Drawing Figures

APPARATUS FOR OBSERVING CARDIAC RHYTHM FREE OF INTERFERING EFFECTS

The present invention relates to apparatus for observing heart-beat rate, and particularly apparatus of that type which is especially applicable for the surveillance of subjects who have implanted cardiac stimulators.

Known cardiac surveillance apparatus determine the heartbeat rate of patients from the R wave of the electrocardiogram. This process does not give complete satisfaction when it is necessary to survey a patient with an implanted cardiac stimulator. Indeed, the R wave of the electrocardiogram and the terminal phase of the stimulating pulse are very similar and it is difficult, if indeed impossible, to distinguish them by an electronic filter. Thus in certain cases, a cardiac frequency meter indicates the frequency set on the cardiac stimulator and not the true frequency of the patient's heart. Certain extreme cases have even been encountered where the cardiac frequency meter indicated a normal cardiac frequency when the heart of the patient had stopped.

The object of the present invention is to avoid this drawback by producing cardiac frequency observation of absolute dependability due to the fact that heatbeats are counted with reference to phenomenon of mechanical rather than electrical origin, namely the contraction of the myocardium shown by the variation of the associated electrical impedance.

For this purpose, the apparatus for observing heartbeats, from which cardiac frequency meter can be operated comprises four electrodes placed on the chest of the subject to be surveyed, namely two electrodes for feeding a high frequency current connected to a high frequency signal generator and, between these, two exploratory electrodes connected to a channel for detecting, filtering and forming the signal for the cardiac frequency meter, this channel being connected to a cardiac rhythm meter proper, characterised in that there is provided a channel for eliminating pulmonary impedance variations connected to the two feed electrodes and delivering a pulmonary rheographic signal and, in the detecting channel, a combining stage in which the pulmonary rheographic signal is subtracted from the rheographic signal.

The cardiac frequency monitor or meter according to the invention resolves all the problems of counting the heartbeats of the electrically stimulated subjects. The dependability of counting which it assures is substantially superior to that of known cardiac frequency meters triggered by the R wave electrocardiographic signal.

With non-stimulated subjects, cardiac frequency meters embodying to the invention assure a precision of counting wholly comparable with that given by known cardiac frequency meters.

The present invention will now be described by way of an illustrative example, with reference to the accompanying drawings in which.

Figure 1:
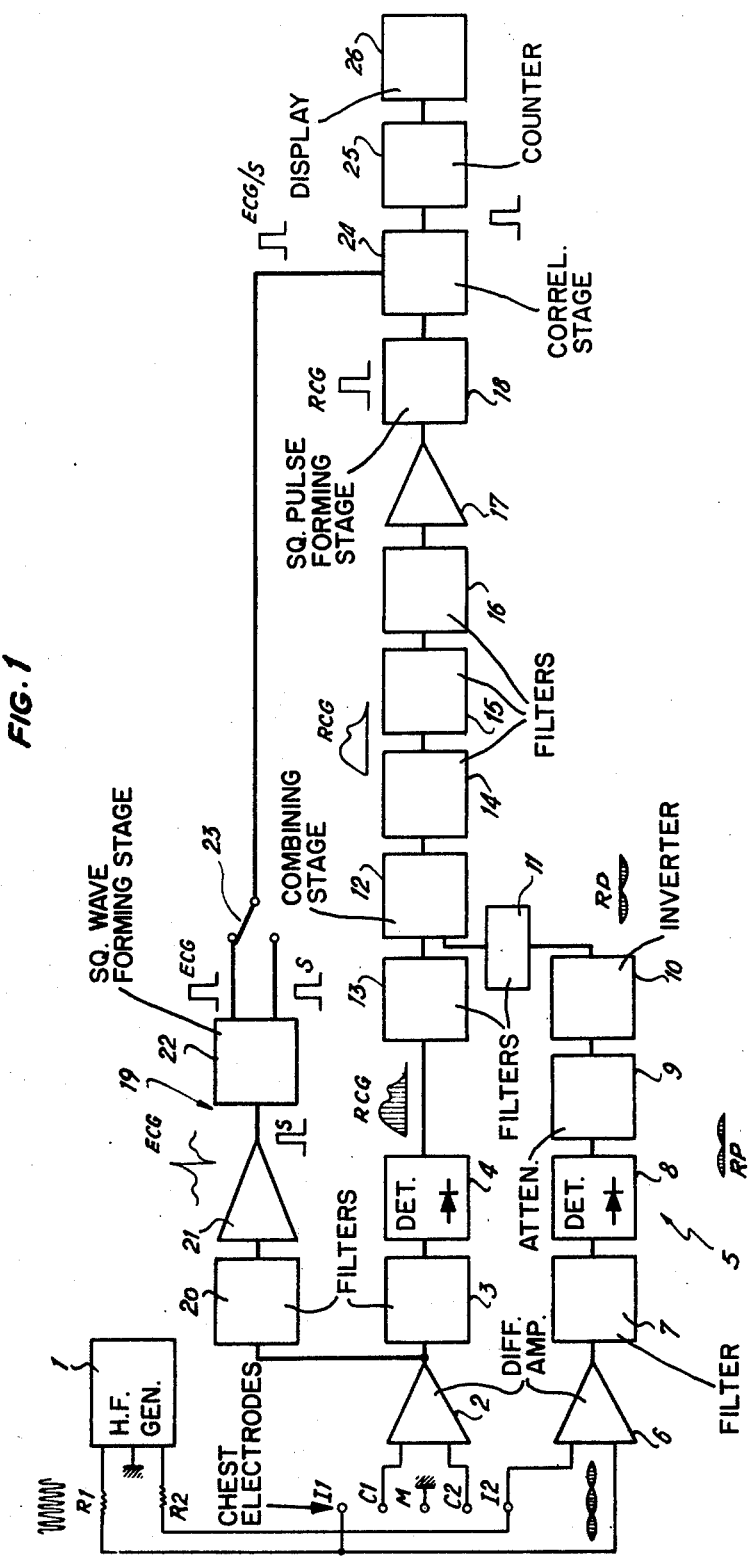
FIG. 1 is a block diagram of a cardiac frequency meter and monitor embodying to the invention.
Figure 2:
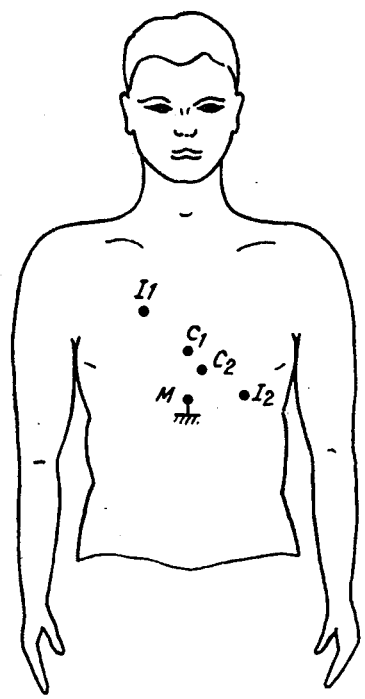
FIG. 2 is a diagram showing the positions of various electrodes on the body of a subject.

The cardiac frequency meter according to the invention works on the principle that the cardiac rheograph consists of the registration of the variations in impedance of the heart during its contractions. The cardiac rheograph feeds a current of constant predetermined frequency, by means of two electrodes $I_1$, $I_2$, adhered to the chest of a patient under surveillance. These electrodes $I_1$, $I_2$, are connected respectively, through current-limiting resistance $R_1$ and $R_2$ (having, for example a value of 2.7k), to two output terminals of a generator 1 supplying an alternating voltage of 25 volts between these terminals. An alternating voltage modified by the variations of cardiac impedance associated with each contraction is recovered between two further electrodes or exploratory electrodes $C_1$ and $C_2$ which are also adhered to the chest of the patient under surveillance between the feeding electrodes $I_1$ and $I_2$. FIG. 2 shows the best position which has been determined for the four electrodes: these latter are positioned on a line merging with the electrical axis of the heart. The high frequency current supplied by the generator 1 is fed by the electrodes $I_1$ and $I_2$, the electrode $I_1$ being placed on the right half of the chest, level with the seventh rib, while the other feeding electrode $I_2$ is placed on the left half of the chest, level with the tenth adjacent rib. The modulated signal is recovered by the exploratory electrodes $C_1$ and $C_2$, the electrode $C_1$ being located on the sternum at the point of intersection with the axis $I_1$, $I_2$, which the electrode $C_2$ is located next to the electrode $C_1$ on the left half of the chest level with the ninth rib. Moreover, a further electrode of mass M is used, the emplacement of which is not critical.

The cardiac frequency meter and monitor embodying the invention uses a rheographic process with four electrodes because this process has the advantage of attenuating the impeding effects of tissue as well as the variations in impedance owing to the occasional absence of contact between the electrodes and the skin, for example during movement of the patient.

The two exploratory electrodes $C_1$ and $C_2$ are connected respectively to two inputs of a differential amplifier 2 with is connected to the input of a filter-cell 3 which eliminates the wave of the electrocardiographic signal, (abbreviated: ECG) as well as the stimulation pulse S of the cardiac stimulator. The signal thus modulated and filtered is fed to a detection stage 4, comprising a diode, this stage supplying the cardiac rheographic signal modulating the high frequency signal.

The high frequency signal collected by the exploratory electrodes $C_1$ and $C_2$ is also modulated by the variations in the pulmonary impedance linked to the respiration of the subject.

Figure 3:
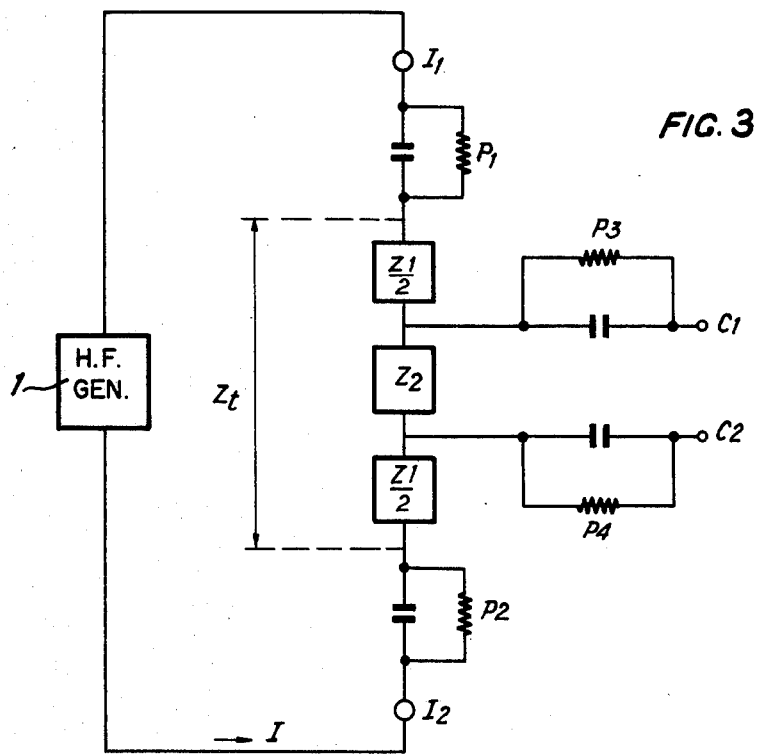
FIG. 3 is an electrical circuit diagram showing the equivalent thoracic and cardiac impedances.

The equivalent circuit diagram shown in FIG. 3 shows that between the feeding electrodes $I_1$ and $I_2$ is located, in series, an impedance P of the skin tissue and of that between the skin and the contacting electrode $I_1$, a total thoracic impedance of $Z_t$, and an inpedance $P_2$, of skin tissue and of the contact between the contacting electrode $I_2$ and the skin. The total thoracic impedance $Z_t$, is altered by a cardiac impedance $Z_2$ which is found between the exploratory electrodes $C_1$ and $C_2$ with the impedance $P_3$ and $P_4$ corresponding to the skin tissue and to the contact impedance between the electrodes and the skin, and one or the other side of the impedance $Z_2$ by the impedances $Z_1/2$, $Z_1$ being defined by $Z_1 = Z_t - Z_2$.

The pulmonary variations in impedance, essentially represented by $Z_1$, have rise-times comparable to those variations of the cardiac impedance. Also, it is difficult to eliminate them by using a simple electronic filter.

In a cardiac frequency meter embodying the invention, the variations of pulmonary impedance are eliminated by means of a channel, designated in this assembly by 5. This channel comprises a differential amplifier 6 with an input of high imput impedance. The two inputs of this amplifier are connected respectively to the electrodes $I_1$ and $I_2$, thereby collecting the pulmonary rheographic signal. The amplifier input 6 is connected to a filter 7 eliminating the electrocardiographic signal and the stimulation pulse, the output of this latter being in turn connected to a detection stage 8 for obtaining the pulmonary rheographic signal RP. The channel comprises an attenuator 9, for bringing the signal thus detected to an identical level to that which is collected between the exploratory electrodes $C_1$ and $C_2$. The output signal of the attemator 9 is fed to an inverter 10, and transmitted across a high frequency filter 11 to an input of a recombination stage 12. This stage receives, at another input, the signal supplied by the detection stage 4, after its passage across another high frequency filter 13.

The combining stage 12 assures the elimination, by subtraction, of the pulmonary rheographic signal RP, and the RCG signal corresponding to the cardiac rheogram comes out from the combining stage 12 separated from the pulmonary signal. It is transmitted to a high pass filter 14, with a Butterworth response, at the end of the elimination of a final residue of the pulmonery signal.

The movements of the patient, also coughing, cause displacement of the electrodes, displacements which are transformed into variations in random impedances, of high amplitude and with rapid rise times.

In order to attenuate these, the cardiac rheographic signal coming from the filter 14 passes through a low-pass filter 15.

It also passes across a bandpass filter 16 designed to eliminate the 50Hz electric power frequency (60Hz in U.S.) that may have been picked up by induction. The cardiac rheographic signal thus filtered is then amplified by an amplifier 17 then shaped into the form of a square wave in a pulse shaping stage 18 in order to make uniform the signals for purposes of counting the cardiac rhythm.

For the exclusion of false signals from the counting of cardiac contraction, an "artifact" or parasite signal can be fed in just after the stage 18. The cardiac frequency meter embodying the invention for that purpose comprises an additional channel, designated in the drawings by 19 and including stages 20, 21, 22 and 23 described below, allowing the establishment of a correlation of the cardiac rheographic signal RCG with the electrocardiographic signal ECG of a subject who does not use a cardiac simulator, or with the stimulation pulse S in the case of a subject using a cardiac stimulator.

The ventricular contraction being the mechanical response to the R wave of the electrocariogram signal ECG or to the stimulation pulse S, it can be seen that the precision of counting of cardiac rhythm by the cardiac rheographic signal is improved if one counts for validity a pulse from the stage 18 only if this pulse is the response to (i.e. has a timed relation to) a wave which is either the R wave of the electrocardiographic signal, or the stimulation pulse.

The electrocardiographic signal ECG is picked-up by the exploratory electrodes $C_1$ and $C_2$. The correlation channel 19 comprises a filter 20 which is connected to the output of the amplifier 2 and which is adapted to eliminate the rheocardiographic signal and, conversely, to allow the electrocardiogram ECG to pass, as well as the stimulation pulse S. The output of this filter is connected to the input of an amplifier 21 which is itself connected to a stage 22 that provides a square wave output. A selection commutator 23 is connected connects, either the output of the electrocardiographic signal ECG, or the output of the stimulation pulse S coming from the stage 22 to one input of a correlation stage 24, which at its other input receives the square wave pulse provided at the output of the stage 18. This correlation stage delivers to its output the validated pulses which are fed to a counter 25 effecting counting of cardiac rhythms in a known manner. This counter is connected to a conventional display apparatus 26 of either analogue or digital type, having the possibility of pre-display brady cardiac and tachycardiac alarms.

It will be understood that the embodiment of the invention which has just been described with reference to the accompanying drawings has been given solely as a non-limiting example, and that numerous modifications can be carried out without departing from the scope of the present invention.

What is claimed is:

1. Apparatus for observing cardiac rhythm free of interfering effects, comprising:
   a high frequency electric wave generator;
   a pair of current feed electrodes connected in circuit with said high frequency generator for placement on the chest of a patient to be examined at locations suitable for forming a pulmonary rheographic signal and for feeding high frequency current through the patient's body;
   a pair of exploratory electrodes for placement on the chest of said patient at locations suitable for picking up a rheocardiographic signal;
   first detecting means connected to said exploratory electrodes for detecting and amplifying said rheocardiographic signal;
   second detecting means connected to said current feed electrodes for detecting said pulmonary rheographic signal and for amplifying it to substantially the same amplitude at which it appears superimposed on said rheocardiographic signal in the output of said first detecting means, and
   subtracting means connected to the outputs of said first and second detecting means for eliminating said superimposed pulmonary rheographic signal from said rheocardiographic signal and providing the latter as an output which is undisturbed by said pulmonary rheographic signal.

2. Apparatus as defined in claim 1, in which said second detecting means comprises a differential amplifier having a high input impedance and having its two inputs respectively connected to the electrodes of said pair of feed electrodes, a filter for eliminating from the output the electrocardiographic signal and, if present, the stimulating pulse, a demodulating stage for detecting the pulmonary rheographic signal, and an attenuator for adjusting the overall amplification of said pulmonary rheographic signal in said second detecting means, and in which apparatus said subtracting means includes an inverter for inverting the polarity of the pulmonary rheographic signal and a signal addition circuit having one input connected to the output of said first detecting means and another input connected to the output of said inverter, for eliminating said superimposed pulmonary rheographic signal from said rheocardiographic signal.

3. Apparatus as defined in claim 1, comprising pulse-forming means responsive to the output of said subtracting means to convert said rheocardiographic signal into a series of uniform pulses, correlation means for eliminating from the output of said pulse-forming means pulses correlated neither with an electrocardiographic signal nor with cardiac stimulation pulse, indicating means responsive to the output of said correlation means for indicating and measuring cardiac rhythm, means responsive to electrocardiographic signals and, if present, cardiac stimulation pulses delivered by connections with said exploratory electrodes for producing correlating pulses for said correlation means, said correlation pulse producing means including a selector switch for selectively connecting to an input of said correlation means either pulses derived from an electrocardiographic signal or pulses corresponding to cardiac stimulation pulses.

4. Apparatus for observing cardiac rhythm free of interfering effects, comprising:

a high frequency electric wave generator;

a pair of current feed electrodes connected in circuit with said high frequency generator for feeding high frequency current through a patient's body;

a pair of exploratory electrodes for placement on the chest of said patient at locations suitable for picking up a rheocardiographic signal;

means connected to said exploratory electrodes for separating said rheocardiographic signal from an electrocardiographic signal and cardiac stimulation pulses and for providing said rheocardiographic signal at a first output and said electrocardiographic signal and, if present, cardiac stimulation pulses, at a second output;

means responsive to said first output of said separating means for demodulating said rheocardiographic signal and for producing a train of pulses representative thereof;

means responsive to said electrocardiographic signal and, if present, said cardiac stimulation pulses, for producing trains of correlating pulses respectively representative thereof and including a selector switch for selecting correlation pulses representative either of said electrocardiographic signal or of cardiac stimulation pulses, and correlation means having a first input connected to the output of said demodulation and pulse-producing means and a second input connected to said selector switch, for eliminating pulses representative of said rheocardiographic signal which are not time-correlated with one of said correlation pulses.

* * * * *